United States Patent [19]

Wirth

[11] Patent Number: 4,772,405

[45] Date of Patent: Sep. 20, 1988

[54] LUBRICANT COMPOSITIONS WHICH CONTAIN SULFUR-CONTAINING PHENOL DERIVATIVES, AND NOVEL SULFUR-CONTAINING PHENOL DERIVATIVES

[75] Inventor: Hermann O. Wirth, Bensheim, Fed. Rep. of Germany

[73] Assignee: Ciba-Geigy Corporation, Ardsley, N.Y.

[21] Appl. No.: 895,985

[22] Filed: Aug. 14, 1986

[30] Foreign Application Priority Data

Aug. 26, 1985 [CH] Switzerland .................... 3659/85

[51] Int. Cl.$^4$ ................ C10M 135/00; C10M 133/00
[52] U.S. Cl. .................... 252/47.5; 252/48.2; 252/78.1; 252/404; 568/41; 568/44; 568/46; 568/47; 524/330; 524/331; 564/440; 564/340; 564/341; 564/355
[58] Field of Search ............ 252/41.5, 48.2, 48.6, 252/78.1, 404; 568/41, 44, 46, 47; 524/330, 331; 564/440

[56] References Cited

U.S. PATENT DOCUMENTS

| | | | |
|---|---|---|---|
| 3,330,804 | 7/1967 | O'Shea | 252/48.2 |
| 3,465,029 | 9/1969 | Beirne | 252/48.2 |
| 3,510,427 | 5/1970 | Worrel | 252/48.2 |
| 3,590,085 | 6/1971 | Braus et al. | 260/609 |
| 3,637,863 | 1/1972 | Braus et al. | 252/48.2 |
| 3,773,722 | 11/1973 | Dexter | 252/47.5 |
| 3,832,328 | 8/1974 | Eggensperger et al. | 252/48.6 |
| 4,021,468 | 5/1977 | Lind | 568/46 |
| 4,108,831 | 8/1978 | Cottman | 260/45.95 |
| 4,147,666 | 4/1979 | Michaelis et al. | 252/48.2 |
| 4,165,333 | 8/1979 | Kline | 260/455 R |
| 4,260,503 | 4/1981 | Michaelis | 252/47.5 |
| 4,511,910 | 4/1985 | Taniguchi et al. | 346/216 |
| 4,612,341 | 9/1986 | Spivack et al. | 252/48.2 |
| 4,618,440 | 10/1986 | Steinberg et al. | 568/41 |

FOREIGN PATENT DOCUMENTS

| | | |
|---|---|---|
| 56172 | 7/1982 | European Pat. Off. |
| 0166696 | 1/1986 | European Pat. Off. |
| 2921620 | 12/1979 | Fed. Rep. of Germany |
| 3414297 | 10/1984 | Fed. Rep. of Germany |
| 2367059 | 5/1978 | France |
| 4961131 | 6/1974 | Japan |
| 4975550 | 7/1974 | Japan |

OTHER PUBLICATIONS

Chem. Abstracts 96:189575n (1982).
Chem. Abstracts 96:199204e (1982).
Fessenden et al., Organic Chemistry, p. 966.

Primary Examiner—William R. Dixon, Jr.
Assistant Examiner—Ellen McAvoy
Attorney, Agent, or Firm—Harry Falber; Edward McC. Roberts

[57] ABSTRACT

The invention relates to compositions comprising a lubricant or a hydraulic fluid and at least one compound of formula I

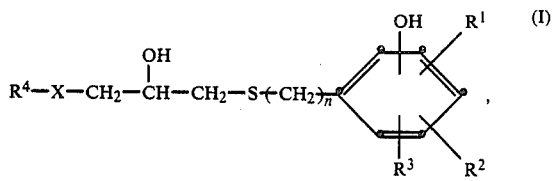

wherein X is —S—, —O—, —CO—O—, —CH$_2$— or —NR$^5$—, where R$^5$ is hydrogen or C$_1$–C$_8$alkyl, n is 0, 1, 2 or 3, R$^1$ and R$^2$ are each independently of the other hydrogen or C$_1$–C$_{12}$alkyl, R$^3$ is hydrogen or methyl, and R$^4$ is C$_1$–C$_{22}$alkyl, C$_5$–C$_8$cycloalkyl, aryl or aryl which is substituted by one or two C$_1$–C$_8$alkyl radicals, or is C$_7$–C$_{12}$aralkyl or the group

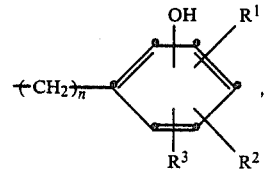

wherein R$^1$, R$^2$, R$^3$ and n have the given meanings.

The sulfur-containing phenol derivatives of formula I are particularly suitable antiwear, extreme pressure and antioxidant additives for mineral and synthetic lubricants and for hydraulic fluids.

The invention further relates to novel phenol derivatives of formula I which are suitable additives for lubricants, hydraulics and elastomers.

22 Claims, No Drawings

LUBRICANT COMPOSITIONS WHICH CONTAIN SULFUR-CONTAINING PHENOL DERIVATIVES, AND NOVEL SULFUR-CONTAINING PHENOL DERIVATIVES

The present invention relates to lubricant and hydraulic fluid compositions which contain sulfur-containing phenol derivatives, to novel sulfur-containing phenol derivatives, and to the use thereof as additives for lubricants, hydraulics and elastomers.

It is customary to treat mineral and synthetic lubricants with additives to improve their performance properties. Particularly useful additives are those that protect the parts which it is desired to lubricate from wear. It is required of these additives that they shall increase the load-carrying capacity of the lubricant, that they shall not have a corrosive action on the metal parts to be protected, and that they shall have good heat resistance.

For this utility it is at the present time preferred to use phosphorus- and sulfur-containing compounds, e.g. the dialkyldithiophosphates disclosed in German Offenlegungsschrift No. 29 21 620.

Sulfur-containing phenol derivatives and the preparation thereof are disclosed e.g. in U.S. Pat. No. 4,108,831, which describes their antioxidant properties in connection with the stabilisation of polymers.

It has now been found that specific sulfur-containing phenol derivatives impart good extreme pressure and antiwear properties to lubricants and hydraulics.

Accordingly, the present invention relates to compositions comprising a lubricant or a hydraulic fluid and at least one compound of formula I

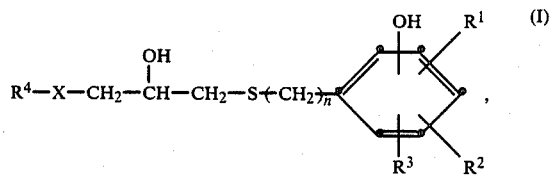

wherein X is —S—, —O—, —CO—O—, —CH$_2$— or —NR$^5$—, where R$^5$ is hydrogen or C$_1$–C$_8$alkyl, n is 0, 1, 2 or 3, R$^1$ and R$^2$ are each independently of the other hydrogen or C$_1$–C$_{12}$alkyl, R$^3$ is hydrogen or methyl, and R$^4$ is C$_1$–C$_{22}$alkyl, C$_5$–C$_8$cycloalkyl, aryl or aryl which is substituted by one or two C$_1$–C$_8$alkyl radicals, or is C$_7$–C$_{12}$aralkyl or the group

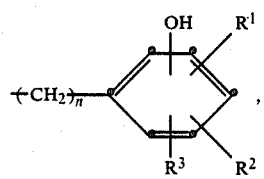

wherein R$^1$, R$^2$, R$^3$ and n have the given meanings.

The preferred meaning of X is —S—, —O—, —CH$_2$— or —CO—O—, with —S— and —O— being particularly preferred and —S— being most preferred. If X is the group —NR$^5$—, R$^5$ is preferably C$_1$–C$_8$alkyl and, most preferably, C$_1$–C$_4$alkyl. If X is —CO—O—, the carbonyl C-atom is attached to the radical R$^4$.

n is an integer having the value 0, 1, 2 or 3, preferably 0 or 1 and, most preferably, 1.

R$^1$ and R$^2$ are preferably straight chain or branched C$_1$–C$_{12}$alkyl substituents selected from the group consisting e.g. of methyl, ethyl, n-propyl, isopropyl, n-butyl, sec-butyl and tert-butyl, pentyl, 1-methylpentyl, n-hexyl, 2-ethyl-n-hexyl, n-heptyl, 1-methylheptyl, n-octyl, straight chain or branched nonyl, decyl, undecyl or dodecyl.

R$^1$ and R$^2$ are each independently of the other preferably methyl or a straight chain or branched, preferably tertiary, C$_4$–C$_8$alkyl radical, with the proviso that at least one of R$^1$ and R$^2$ must be said tertiary alkyl radical.

In a particularly preferred embodiment of the lubricant compositions of this invention, R$^1$ and R$^2$ in compounds of formula I are each independently of the other methyl or tert-butyl, with the proviso that at least one of R$^1$ and R$^2$ must be tert-butyl.

The radicals R$^1$ and R$^2$ may be identical or different and are preferably identical.

The preferred meaning of R$^3$ is hydrogen.

The most preferred lubricant compositions are those which contain a compound of formula I, wherein R$^1$ and R$^2$ are each independently of the other methyl or tert-butyl, and R$^3$ is hydrogen.

R$^4$ as C$_1$–C$_{22}$alkyl is a straight chain or branched C$_1$–C$_{22}$alkyl substituent which may be selected from the group consisting e.g. of methyl, ethyl, n-propyl, isopropyl, n-butyl, sec-butyl or tert-butyl, pentyl, 1-methylpentyl, n-hexyl, 2-ethyl-n-hexyl, n-heptyl, 1-methylheptyl, n-octyl, straight chain or branched nonyl, decyl, undecyl, dodecyl, tridecyl, tetradecyl, pentadecyl, hexadecyl, octadecyl, eicosyl or docosyl.

R$^4$ is preferably a straight chain or branched C$_2$–C$_{12}$alkyl radical and is most preferably a tertiary C$_4$–C$_9$alkyl radical, with e.g. tert-octyl being understood as meaning a radical as defined for tertiary octylmercaptan in Ullmanns Enzyklopädie der technischen Chemie, 4th Edition, Vol. 23, pp. 181–182, Verlag Chemie, Weinheim, so that X is attached to a tertiary carbon atom.

R$^4$ as C$_5$–C$_8$cycloalkyl is e.g. cyclopentyl, cyclohexyl, 4-methylcyclohexyl or cyclooctyl. Preferably R$^4$ is C$_5$–C$_6$cycloalkyl.

R$^4$ as aryl substituted by one or two C$_1$–C$_8$alkyl radicals is preferably phenyl which is substituted by one or two straight chain or branched C$_1$–C$_8$alkyl radicals, e.g. by one or two members selected from the group consisting e.g. of methyl, ethyl, n-propyl, iso-propyl, n-butyl, sec-butyl or tert-butyl, n-pentyl, 1-methylpentyl, n-hexyl, 2-ethyl-n-hexyl, n-heptyl, 1-methylheptyl, n-octyl, sec-octyl and tert-octyl. R$^4$ is preferably a phenyl radical which is substituted by one or two C$_1$–C$_4$alkyl radicals, with the proviso that, in the case of substitution with two C$_1$–C$_4$alkyl radicals, said radicals may be identical or different, preferably identical.

R$^4$ as C$_7$–C$_{12}$aralkyl may be e.g. a benzyl, α-methylbenzyl, α,α-di-methylbenzyl, 1-phenylethyl, 2-phenylethyl, 2-phenylpropyl, 3-phenylpropyl, 4-phenylbutyl or phenylhexyl radical. R$^4$ is preferably a C$_7$–C$_{10}$aralkyl substituent and, most preferably, a benzyl radical.

R$^4$ may also be the group

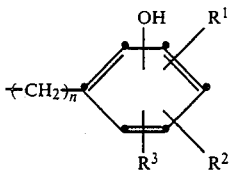

wherein $R^1$, $R^2$, $R^3$ and n have the given meanings.

$R^4$ is preferably $C_1$-$C_{22}$alkyl, in particular $C_2$-$C_{18}$alkyl and, most preferably, $C_2$-$C_{12}$alkyl, or is $C_5$-$C_8$cycloalkyl, in particular $C_5$-$C_6$cycloalkyl and, most preferably, $C_6$cycloalkyl. First and foremost, $R^4$ is $C_4$-$C_{12}$alkyl.

In compounds of formula I, the phenolic hydroxyl group may preferably be located in 2-, 3- or 4-position to the radical $R^4$—X—$CH_2$—CH(OH)—$CH_2$—S—$(CH_2)_n$—, with the 2- and 4-positions, in particular the 4-position, being preferred.

The radicals $R^1$ and $R^2$ are preferably located in ortho-position to the phenolic hydroxyl group.

Preferred compositions are those comprising a lubricant and at least one compound of formula I, wherein X is —S—, —O—, —$CH_2$— or —CO—O—, preferably —S— or —O—, most preferably —S—, n is 0 or 1, $R^1$ and $R^2$ are each independently of the other hydrogen, methyl or tertiary $C_4$-$C_8$alkyl, $R^3$ is hydrogen and $R^4$ is $C_2$-$C_{12}$alkyl, $C_5$-$C_6$cycloalkyl, aryl or aryl substituted by one or two $C_1$-$C_4$alkyl radicals, or is $C_7$-$C_{10}$aralkyl.

The most preferred compositions are those comprising a lubricant and at least one compound of formula I, wherein X is —S—, —O—, —$CH_2$— or —CO—O—, n is 0 or 1, the phenolic hydroxyl group is in 4-position, $R^1$ and $R^2$ are located in positions ortho to the phenolic hydroxyl group and are each independently of the other $C_1$-$C_6$alkyl, $R^3$ is hydrogen and $R^4$ is $C_2$-$C_{12}$alkyl or cyclohexyl.

Some of the compounds of formula I are novel. The invention therefore also relates to novel compounds of formula I, wherein X is —S—, —O—, —CO—O— or —$CH_2$—, n is an integer having the value 0, 1, 2 or 3, $R^1$ and $R^2$ are each independently of the other hydrogen or $C_1$-$C_{12}$alkyl, $R^3$ is hydrogen or methyl, and $R^4$ is $C_1$-$C_{22}$alkyl, $C_5$-$C_8$cycloalkyl, aryl or aryl substituted by one or two $C_1$-$C_8$alkyl radicals, or is $C_7$-$C_{12}$aralkyl or, if n is 1, 2 or 3, is also the group

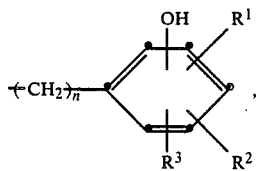

wherein $R^1$, $R^2$ and $R^3$ have the given meanings. The meanings and preferred meanings of $R^1$, $R^2$, $R^3$, $R^4$, X and n in novel compounds of formula I are those previously stated above.

Preferred compounds of formula I are those wherein X is —S—, —O—, —$CH_2$— or —CO—O—, n is 0 or 1, $R^1$ and $R^2$ are each independently of the other hydrogen, methyl or tertiary $C_4$-$C_8$alkyl, $R^3$ is hydrogen and $R^4$ is $C_2$-$C_{12}$alkyl, $C_5$-$C_6$cycloalkyl, aryl or aryl substituted by one or two $C_1$-$C_4$alkyl radicals, or is $C_7$-$C_{10}$aralkyl.

Preferred novel compounds of formula I are likewise those wherein $R^4$ is $C_1$-$C_{22}$alkyl (preferably $C_2$-$C_{18}$alkyl and, most preferably, $C_2$-$C_{12}$alkyl), or $C_5$-$C_8$cycloalkyl (preferably $C_5$-$C_6$cycloalkyl and, most preferably, $C_6$cycloalkyl), with $C_4$-$C_{12}$alkyl being particularly preferred; as well as those wherein X is —O— or —S—, preferably —S—; as well as those wherein the phenolic hydroxyl group is in 4-position and, most particularly, those wherein $R^1$ and $R^2$ are each independently of the other methyl or tert-butyl and are located in both positions ortho to the hydroxyl group. At least one of these ortho-positions will preferably carry a tert-butyl radical.

Particularly preferred novel compounds of formula I are those wherein X is —S—, —O—, —$CH_2$— or —CO—O—, n is 0 or 1, the phenolic hydroxyl group is in 4-position, $R^1$ and $R^2$ are located in the positions ortho to the phenolic hydroxyl group and are each independently of the other $C_1$-$C_6$alkyl, $R^3$ is hydrogen and $R^4$ is $C_2$-$C_{12}$alkyl or cyclohexyl.

Representative examples of compounds of formula I are:

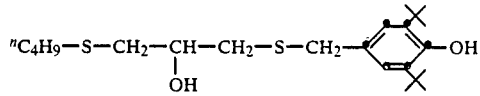

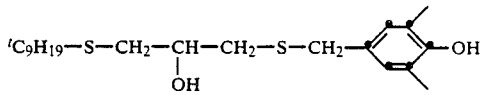

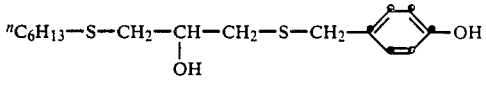

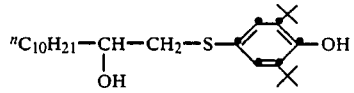

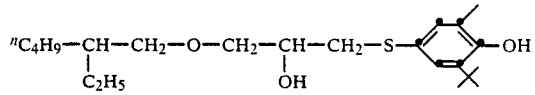

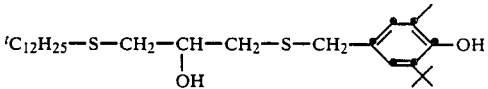

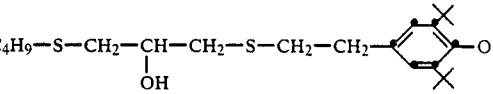

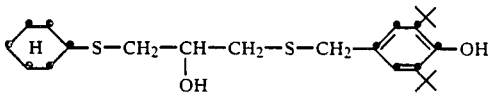

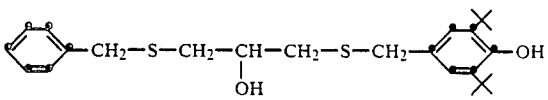

-continued

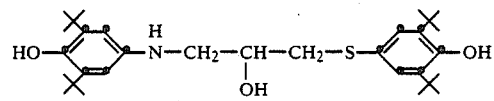

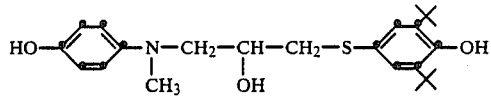

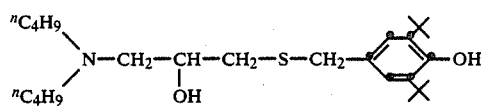

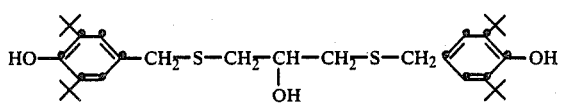

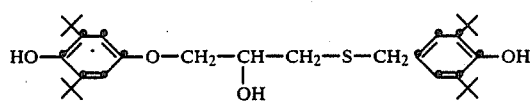

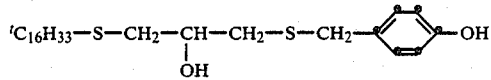

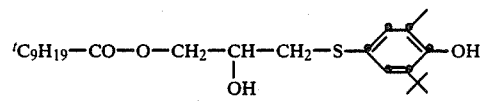

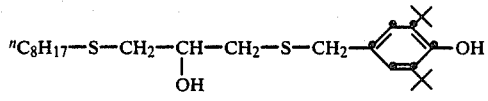

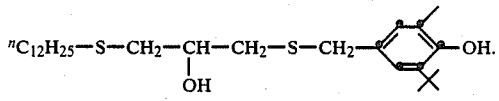

The compounds of formula I can be obtained in a manner known per se, for example by reacting a glycidyl compound of formula II

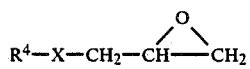 (II)

with a sulfide compound of formula III

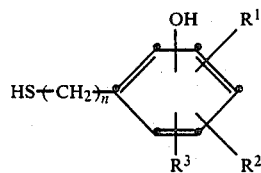 (III)

The compounds of formula I can also be prepared for example by reacting a compound

with a phenolic glycidylthioether derivative of formula IV

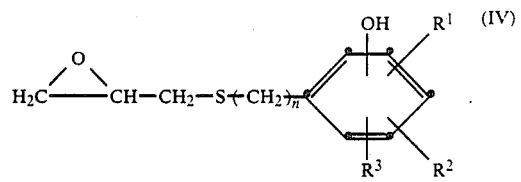 (IV)

In the above formulae, $R^1$, $R^2$, $R^3$, $R^4$, X and n are each as defined previously.

The compounds of formula II can be prepared in a manner known per se, for example in accordance with the following reaction:

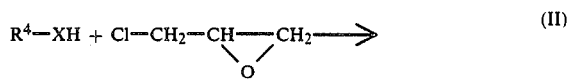 (II)

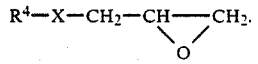

The compounds of formula III are disclosed e.g. in U.S. Pat. No. 4,108,831 or 4,165,333, or they can be prepared e.g. in accordance with European patent application EP-A 35472 or as described by G. Scott in Mater. Plast. Elastomeri 1977, pp. 298-301.

Some of the compounds of formula IV are described e.g. by T. Fujisawa et al., in J. Polym. Sci., Polym. Lett. Ed., Vol. 12, pp. 557-559 (1974), or they can be prepared by analogous methods.

A further possibility of obtaining the compounds of formula I, wherein n is 1, comprises reacting a phenol of formula

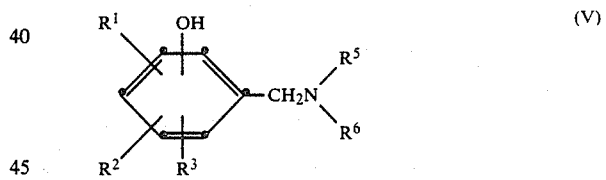 (V)

with a compound of formula $$R_4-X-CH_2-CH(OH)-CH_2SH. \quad (VI)$$

This reaction too is known per se and is described e.g. in U.S. Pat. No. 2,417,118. The starting materials of formulae V and VI are also known and can be obtained by conventional methods. The compounds of formula V can be prepared e.g. by reacting a phenol of formula

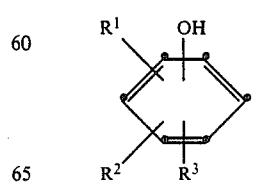

with formaldehyde or a formaldehyde donor and an amine of formula $HNR^5R^6$, wherein $R^5$ and $R^6$, as in formula V, are e.g. hydrogen, alkyl (e.g. $C_1$–$C_6$alkyl), substituted alkyl (e.g. by OH or CN), benzyl, cycloalkyl, or together with the nitrogen atom to which they are attached form a 5- or 6-membered saturated heterocycle. $R^5$ and $R^6$ are preferably $C_1$–$C_6$alkyl.

The sulfur-containing phenol derivatives of this invention constitute lubricant and hydraulic fluid additives which are distinguished by good extreme pressure, antiwear and antioxidant properties. The compounds of formula I are effective even when incorporated in lubricants or hydraulics in very minor amounts. Thus, for example, mineral and synthetic lubricant oils and mixtures thereof which contain 0.01 to 5% by weight, preferably 0.05 to 3% by weight, based on the lubricant, of a compound of formula I have excellent properties, in particular antiwear properties. The suitable lubricants are known to the skilled person and are described e.g. in "Schmierstoffe und verwandte Produkte" (Verlag Chemie, Weinheim, 1982).

The additives of formula I are especially suitable for use in non-automatic and, preferably, in automatic, transmissions of automobiles. Further, they are most effective when used in motor oils, diesel engine oils or turbine oils.

Hence the invention also relates to the use of compounds of formula I as well as of novel compounds of formula I as additives for mineral and synthetic lubricants. In connection with this utility, $R^1$, $R^2$, $R^3$, $R^4$, X and n have the preferred meanings indicated previously.

The lubricant and hydraulic fluid compositions of this invention may contain other additives which are incorporated to enhance the basic properties of lubricants still further. These further basic additives comprise: antioxidants, metal deactivators, rust inhibitors, viscosity index improvers, pour-point depressors, dispersants, surfactants and other extreme pressure additives and antiwear additives.

EXAMPLES OF PHENOLIC ANTIOXIDANTS

1. Alkylated monophenols
2,6-di-tert-butyl-4-methylphenol
2,6-di-tert-butylphenol
2-tert-butyl-4,6-dimethylphenol
2,6-di-tert-butyl-4-ethylphenol
2,6-di-tert-butyl-4-n-butylphenol
2,6-di-tert-butyl-4-sec-butylphenol
2,6-dicyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol
o-tert-butylphenol 2. Alkylated hydroquinones
2,6-di-tert-butyl-4-methoxyphenol
2,5-di-tert-butyl-hydroquinone
2,5-di-tert-amyl-hydroquinone
2,6-diphenyl-4-octadecyloxyphenol 3. Hydroxylated thiodiphenyl ethers
2,2'-thio-bis(6-tert-butyl-4-methylphenol)
2,2'-thio-bis(4-octylphenol)
4,4'-thio-bis(6-tert-butyl-3-methylphenol)
4,4'-thio-bis(6-tert-butyl-2-methylphenol)

4. Alkylidene bisphenols
2,2'-methylene-bis(6-tert-butyl-4-methylphenol)
2,2'-methylene-bis(6-tert-butyl-4-ethylphenol)
2,2'-methylene-bis[4-methyl-6-(α-methylcyclohexyl)phenol]
2,2'-methylene-bis(4-methyl-6-cyclohexylphenol)
2,2'-methylene-bis(6-nonyl-4-methylphenol)
2,2'-methylene-bis(4,6-di-tert-butylphenol)
2,2'-ethylidene-bis(4,6-di-tert-butylphenol)
2,2'-ethylidene-bis(6-tert-butyl-4-isobutylphenol)
2,2'-methylene-bis[6-(α-methylbenzyl)-4-nonylphenol]
2,2'-methylene-bis[6-(α,α-dimethylbenzyl)-4-nonylphenol]
4,4'-methylene-bis-(2,6-di-tert-butylphenol)
4,4'-methylene-bis(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5'-tert-butyl-4'-hydroxy-2'-methylphenyl)-3-n-dodecylmercaptobutane
ethylene glycol bis[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methylbenzyl)-6-tert-butyl-4-methylphenyl]terephthalate.

5. Benzyl compounds
1,3,5-tris(3,5-di-tert-butyl-4-hydroxybenzyl)-2,4,6-trimethylbenzene
bis(3,5-di-tert-butyl-4-hydroxybenzyl)sulfide
isooctyl 3,5-di-tert-butyl-4-hydroxybenzylmercaptoacetate
bis(4-tert-butyl-3-hydroxy-2,6-dimethylbenzyl)dithiolterephthalate
1,3,5-tris(3,5-di-tert-butyl-4-hydroxybenzyl)isocyanurate
1,3,5-tris(4-tert-butyl-3-hydroxy-2,6-dimethylbenzyl)isocyanurate
dioctadecyl 3,5-di-tert-butyl-4-hydroxybenzylphosphonate
calcium salt of monoethyl 3,5-di-tert-butyl-4-hydroxybenzylphosphonate.

6. Acylaminophenols
4-hydroxylauric anilide
4-hydroxystearic anilide
2,4-bisoctylmercapto-6-(3',5'-tert-butyl-4'-hydroxyanilino)-s-triazine
octyl N-(3,5-di-tert-butyl-4-hydroxyphenyl)carbamate 7. Esters of β-(3,5-di-tert-butyl-4-hydroxyphenyl)propionic acid with monohydric or polyhydric alcohols, for example with methanol, octadecanol, 1,6-hexanediol, neopentyl neopentyl glycol, thiodiethylene glycol, diethyleneglycol, triethylene glycol, pentaerythritol, trishydroxyethyl isocyanurate, dihydroxyethyloxalyldiamide.

8. Esters of β-(5-tert-butyl-4-hydroxy-3-methylphenyl)propionic acid
with monohydric or polyhydric alcohols, for example methanol, octadecanol, 1,6-hexanediol, neopentylglycol, thiodiethyleneglycol, diethylene glycol, triethyleneglycol, pentaerytritol, trishydroxyethyl isocyanurate or dihydroxyethyl oxalyldiamide.

9. Amides of β-(3,5-di-tert-butyl-4-hydroxyphenyl)propionic acid, for example
N,N'-bis(3,5-di-tert-butyl-4-hydroxyphenylpropionyl)hexamethylenediamine
N,N'-bis(3,5-di-tert-butyl-4-hydroxyphenylpropionyl)trimethylenediamine
N,N'-bis(3,5-di-tert-butyl-4-hydroxyphenylpropionyl)hydrazine.

Examples of amine antioxidants:
N,N'-diisopropyl-p-phenylenediamine
N,N'-di-sec-butyl-p-phenylenediamine
N,N'-bis(1,4-dimethylpentyl)-p-phenylenediamine N,N'-bis(1-ethyl-3-methylpentyl)-p-phenylenediamine
N,N'-bis(1-methylheptyl)-p-phenylenediamine
N,N'-diphenyl-p-phenylenediamine
N,N'-di(naphthyl-2-)-p-phenylenediamine
N-isopropyl-N'-phenyl-p-phenylenediamine
N-(1,3-dimethylbutyl)-N'-phenyl-p-phenylenediamine
N-(1-methylheptyl)-N'-phenyl-p-phenylenediamine
N-cyclohexyl-N'-phenyl-p-phenylenediamine
bis-4-(toluenesulfonamidophenyl)amine
N,N'-dimethyl-N,N'di-sec-butyl-p-phenylenediamine
diphenylamine
4-isopropoxydiphenylamine
N-phenyl-1-naphthylamine
N-phenyl-2-naphthylamine
octylated diphenylamine
4-n-butylaminophenol
4-n-butyrylaminophenol
4-nonanonylaminophenol
4-dodecanoylaminophenol
4-octadecanoylaminophenol
di-(4-methoxyphenyl)amine
2,6-di-tert-butyl-4-dimethylaminomethylphenol
2,4-diaminodiphenylmethane
4,4'-diaminodiphenylmethane
N,N,N'N'-tetramethyl-4,4'-diaminodiphenylmethane
1,2-di(phenylamino)ethane
1,2-di-[(2-methylphenyl)amino]ethane(o-tolyl)biguanide
di-[4-(1',3'-dimethylbutyl)phenyl]amine
tert-octylated N-phenyl-1-naphthylamine
mixture of mono- and dialkylated tert-butyl- and tert-octyldiphenylamines.

Examples of metal deactivators are:

for copper, e.g.: triazole, benzotriazole and derivatives thereof, 2-mercaptobenzotriazole, 2,5-dimercaptothiadiazole, salicylidene propylenediamine, salts of salicylaminoguanidine.

Examples of rust inhibitors are:

(a) Organic acids, the esters, metal salts and anhydrides thereof, e.g.: N-oleylsarcosine, sorbitan monooleate, lead naphthenate, dodecenylsuccinic anhydride, monoalkenyl succinate, 4-nonylphenoxyacetic acid.

(b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, e.g. substituted imidazolines and oxazolines.

(c) Phosphorous-containing compounds, for example: amine salts of phosphoric acid partial esters.

(d) Sulfur-containing compounds, for example: barium dinonylnaphthalenesulfonates, calcium petroleum sulfonates.

Examples of viscosity index improvers are:

polymethylacrylates, vinyl pyrrolidone/methacrylate copolymers, polybutene, olefin copolymers, styrene/acrylate copolymers.

Examples of pour-point depressors are:

polymethacrylates, alkylated naphthalene derivatives.

Examples of dispersants/surfactants are:

polybutenylsuccinimides, polybutenylphosphonic acid derivatives, basic magnesium, calcium and barium sulfonates and phenolates.

Examples of anti-wear additives are:

compounds which contain sulfur and/or phosphorous and/or halogen, such as sulfurised vegetable oils, zinc dialkyldithiophosphates, tritolylphosphate, chlorinated paraffins, alkyl disulfides and aryl disulfides.

The novel compounds of formula I are furthermore very suitable additives (stabilisers) for elastomers, which they stabilise against deterioration and against degradation reactions caused in particular by oxidative processes. In addition to relating to their use as additives for lubricants, the present invention hence also relates to the use of the novel compounds of formula I as additives (stabilisers) for elastomers. Besides relating to lubricant compositions which contain the novel compounds of formula I, the present invention further relates to compositions which comprise an elastomer and at least one novel compound of formula I.

Examples of suitable elastomers are the following materials:

(A) Polydienes such as polybutadiene, polyisoprene or polychloroprene; block polymers such as styrene/butadiene/styrene, styrene/isoprene/styrene or acrylonitrile/butadiene copolymers.

(B) Copolymers of monoolefins and diolefins with each other or with other vinyl monomers, for example ethylene/alkyl acrylates, ethylene/alkyl methacrylates, ethylene/vinyl acetate or ethylene/acrylic acid copolymers and terpolymers of ethylene with propylene and a diene such as hexadiene, dicyclopentadiene or ethylidenenorbornene.

(C) Halogen-containing polymers, e.g. polychloroprene, chlorinated rubber, chlorinated or sulfochlorinated polyethylene, epichlorohydrin homo- and copolymers, chlorotrifluoroethylene copolymers, polymers from halogen-containing vinyl compounds, e.g. polyvinylidene chloride, polyvinylidene fluoride, as well as copolymers thereof, for example vinyl chloride/vinylidene chloride, vinyl chloride/vinyl acetate or vinylidene chloride/vinyl acetate copolymers.

(D) Polyurethanes which are derived from hydroxyl-terminated polyethers, polyesters and polybutadiene on the one hand and from aliphatic or aromatic polyisocyanates on the other, as well as precursors thereof.

(E) Natural rubber.

(F) Mixtures (polyblends) of the above-mentioned polymers.

(G) Aqueous emulsions of natural or synthetic rubbers, e.g. natural latex or latices of carboxylated styrene/butadiene copolymers.

These elastomers may be in the form of latices and can be stabilised as such.

Preferred compositions are those wherein the elastomer is a polydiene such as polybutadiene rubber, a halogenated polymer such as polyvinylidene fluoride, or a polyurethane.

The compositions of this invention conveniently contain 0.01 to 10% by weight, preferably 0.05 to 5.0% by weight, of a novel compound of formula I, based on the elastomer. Mixtures of stabilisers of formula I can also be used.

In practice, the novel phenolic compounds of formula I can also be used in elastomers together with other stabilisers.

Examples of further additives with which the stabilisers employed in the practice of this invention may be used are:

1. Further antioxidants

Examples of suitable antioxidants are those listed in classes (1) to (9) under the heading "Examples of further phenolic antioxidants" in connection with the recitation of optional components of the lubricant compositions of this invention.

2. UV absorbers and light stabilisers 2.1. 2-(2'-Hydroxyphenyl)benztriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example phenyl salicylate, 4-tert-butyl-phenylsalicilate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, and hexadecyl 3,5-di-tert-butyl-4-hydroxybenzoate.

2.4. Acrylates, for example ethyl α-cyano-β,β-diphenylacrylate, methyl 2-carbomethoxycinnamate, methyl α-cyano-β-methyl-p-methoxycinnamate, butyl α-cyano-β-methyl-p-methoxy-cinnamate, methyl α-carbomethoxy-p-methoxy-cinnamate and N-(β-carbomethoxy-β-cyanovinyl)-2-methylindoline.

2.5 Nickel compounds, for example nickel complexes of 2,2'-thiobis[4-(1,1,3,3-tetramethylbutyl)phenol] such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methyl-phenyl undecyl ketoneoxime, nickel complexes of 1-phenyl-4-lauroyl-5-hydroxypyrazole, with or without additional ligands.

2.6 Sterically hindered amines, for example bis(2,2,6,6-tetramethylpiperidyl)sebacate, bis(1,2,2,6,6-pentamethylpiperidyl)sebacate, bis-(1,2,2,6,6-pentamethylpiperidyl)n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethylpiperidyl)-hexamethylenediamine and 4-tert-octylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetracarboxylic acid, 1,1'-(1,2-ethanediyl)-bis(3,3,5,5-tetramethylpiperazinone).

2.7. Oxalyl diamides, for example 4,4'-dioctyloxyoxanilide, 2,2'-dioctyloxy-5,5'-di-tert-butyloxanilide, 2,2'-di-dodecyloxy-5,5'-di-tert-butyloxanilide, 2-ethoxy-2'-ethyloxanilide, N,N'-bis(3-di-methylaminopropyl)oxalamide, 2-ethoxy-5-tert-butyl-2'-ethyloxanilide and a mixture thereof with 2-ethoxy-2'-ethyl-5,4'-di-tert-butyloxanilide, and mixtures of ortho- and para-methoxy-disubstituted and mixtures of o- and p-ethoxy-disubstituted oxanilides.

3. Metal deactivators, for example N,N'-diphenyloxalyl diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bisbenzylideneoxalic dihydrazide.

4. Phosphites and phosphonites, for example triphenyl phosphite, diphenylalkyl phosphites, phenyldialkyl phosphites, tri(nonylphenyl)phosphite, trilauryl phosphite, trioctadecyl phosphite, distearylpentaerythritol diphosphite, tris(2,4-di-tert-butylphenyl)phosphite, diisodecylpentaerythritol diphosphite, di-(2,4-di-tert-butylphenyl)pentaerythritol diphosphite, tristearylsorbitol triphosphite, tetrakis(2,4-di-tert-butylphenyl)-4,4'-biphenylene diphosphonite, 3,9-bis-(2,4-di-tert-butylphenoxy-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zincdibutyldithiocarbamate, dioctadecyldisulfide, pentaerythritoltetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, manganese stearate, sodium ricinoleate and potassium palmitate, antimony pyrocatechoate or tin pyrocatechoate.

8. Nucleating agents, for example 4-tert-butylbenzoic acid, adipic acid, diphenylacetic acid.

9. Fillers and reinforcing agents, for example calcium carbonate, silicates, glass fibres, asbestos, talcum, kaolin, mica, barium sulfate, metal oxides and hydroxides, carbon black, graphite.

10. Other additives, for example plasticisers, lubricants, emulsifiers, pigments, fluorescent whitening agents, flame retardants, antistatic agents, blowing agents.

Incorporation of the novel compounds of formula I in the polymer can be effected, for example, by blending the compounds and further optional additives by methods conventionally employed in the art, before or during the manufacture of articles shaped from said polymer, or also by applying the dissolved or dispersed compounds to the polymer, with or without subsequent evaporation of the solvent. The novel compounds of formula I may also be added to the plastics to be stabilised in the form of a masterbatch which contains said compounds, for example in a concentration of 2.5 to 25% by weight.

The compositions of the invention can be used in a very wide range of forms, for example as films, filaments, ribbons, moulding compositions, profiles, or as binders for varnishes, adhesives or putties.

The following Examples illustrate the invention in more detail.

EXAMPLE 1

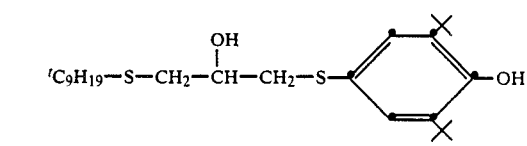

23.8 g (0.1 mole) of 4-mercapto-2,6-di-tert-butylphenol are dissolved in 25 ml of toluene and, after addition of a trace of sodium hydride, the solution is heated to 80° C. With stirring, 22.7 g (0.105 mole) of tert-nonyl glycidylthioether are then added dropwise. The reaction mixture is stirred for 30 minutes at 80° C. and filtered. The filtrate is concentrated in a rotary evaporator, affording 43.1 g (95% of theory) of a viscous liquid with a refractive index $n_{20}^D$: 1:5369.

EXAMPLES 2–6

Further compounds listed in Table 1 are prepared in accordance with Example 1.

A catalytic amount of sodium hydride is added to 15.8 g (0.075 mole) of 4-mercaptomethyl-2-methyl-6-tert-butylphenol in a 100 ml two-necked flask. The contents of the flask are heated to 80° C. and then 16.2 g (0.08 mole) of n-octyl glycidylthioether are added gradually at this temperature, with stirring. The reaction mixture is subsequently stirred for 30 minutes at 80° C. and then worked up.

TABLE 1

| Example | Formula | Refractive index $n_{20}^D$ | Melting point (°C.) |
|---|---|---|---|
| 2 | 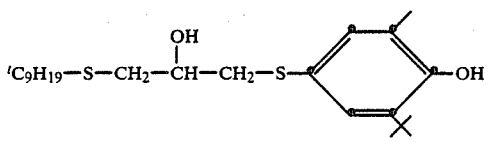 | 1.5458 | |
| 3 | 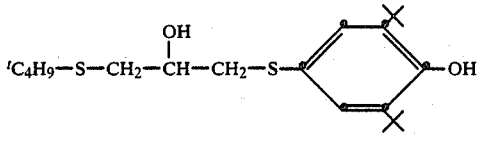 | | 113–115 |
| 4 | 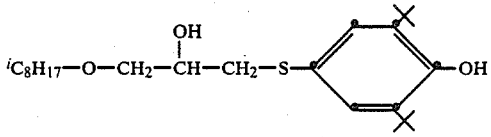 | 1.5166 | |
| 5 | 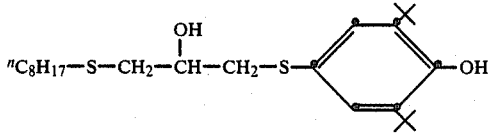 | 1.5327 | |
| 6 | 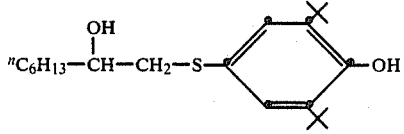 | | 62–64 |

EXAMPLE 7

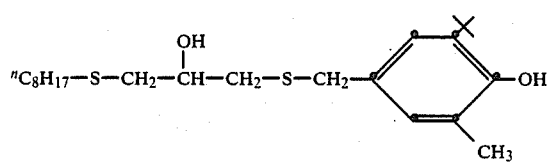

Yield: 32.1 g (100% of theory) of a viscous liquid with a refractive index $n_{20}^D$: 1.5387.

EXAMPLES 8–9

Further compounds listed in Table 2 are prepared in accordance with Example 7.

TABLE 2

| Example | Formula | Refractive index $n_{20}^D$ |
|---|---|---|
| 8 | 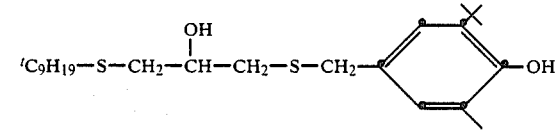 | 1.5418 |

TABLE 2-continued

| Example | Formula | Refractive index $n_{20}^D$ |
|---|---|---|
| 9 | 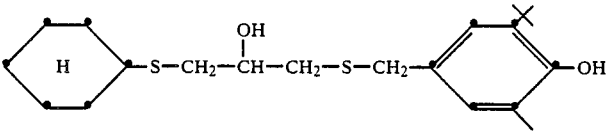 | 1.5666 |

EXAMPLE 10

A 300 ml three-necked flask equipped with thermometer, nitrogen inlet, stirrer and condenser is charged with 19.5 g of 2-tert-butyl-6-methyl-4-dimethylaminophenol, 23.4 g of 1-mercapto-3-tert-dodecylthio-2-hydroxypropane and 105 ml of toluene. The mixture is heated to 100°–105° C. and stirred for a total of 30 hours. The reaction mixture is then washed with 2×50 ml of 1N HCl and with 3×75 ml of water. The organic phase is dried over sodium sulfate and, after removal of the drying agent, the toluene is distilled off under vacuum (0.2 mm) at 60°–65° C., affording 36.6 g (98% of theory) of the compound of formula

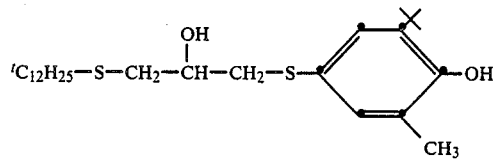

as a pale yellow syrup. The H¹NMR spectrum is consistent with the expected structural formula.

EXAMPLES 11–17

Further compounds listed in Table 3 are prepared in accordance with Example 10.

TABLE 3

| Example | $R_1$ | R | Yield (%) | Physical form |
|---|---|---|---|---|
| 11 | $^tC_4H_9$ | $^tC_{12}H_{25}S-$ | 95 | amber syrup |
| 12 | $CH_3$ | $^tC_{12}H_{25}S-$ | 98 | yellow syrup |
| 13 | $^tC_4H_9$ | $^iC_8H_{17}O-$ | 94 | amber syrup |
| 14 | $CH_3$ | $^iC_8H_{17}O-$ | 95 | yellow syrup |
| 15 | $^tC_4H_9$ | $C_8-C_{10}H_{17}-H_{21}\underset{\underset{O}{\parallel}}{C}-O-$ | 89 | amber syrup |
| 16 | $CH_3$ | $C_8-C_{10}H_{17}-H_{21}\underset{\underset{O}{\parallel}}{C}-O-$ | 86 | yellow syrup |
| 17 | $^tC_4H_9$ | $^tC_9H_{19}S-$ | 82 | amber syrup |

EXAMPLE 18

The weld load (WL) and the wear scar diameter (WSD) are determined using the Shell four-ball machine (IP 239/73, Extreme Pressure and Wear Lubricant Test for Oils and Greases, Four-Ball Machine) according to the ASTM standard method D 2783-81.

WL=weld load: the load at which the 4 balls become welded together within 10 seconds WSD=wear scar diameter: the average diameter of the scars produced on the 3 immobile balls after 1 hour at a load of 400N.

The base oil is Catenex ® P 941 (ex Shell). The test results are reported in Table 4.

TABLE 4

| Additive Example | Concentration [% by weight] | WL [N] | WSD [mm] |
|---|---|---|---|
| Base oil without additive | — | 1350 | 0.85 |
| 8 | 1.0 | 1600 | 0.55 |
|   | 2.5 | 1800 | — |
| 9 | 1.0 | 1600 | 0.60 |
|   | 2.5 | 1600 | — |

EXAMPLE 19

Stabilization of polybutadiene rubber (oven ageing)

100 g of polybutadiene (Diene ® 35, ex Firestone) are blended homogeneously on a two-roll mill at 50° C. for 6 minutes with 0.25% of the stabiliser to be tested. Samples having a thickness of 10 mm are pressed at 80° C. from the rolled sheet. A further sample is prepared in the same manner without a stabiliser.

The stability test is carried out by subjecting the samples to heat ageing in a circulating air oven. The criterion for determining the stability of the samples is the gel content formed during oven ageing.

The gel content increases rapidly after an induction period. The time in which a sample exhibits a gel content of 15% is taken as the arbitrary definition of the induction period. This induction period is measured in days. The results are reported in Table 5.

TABLE 5

| Compound of Example | Reduction time (in days) until the gel content is 15% |
|---|---|
| without | <7 |
| 4 | 17 |
| 13 | 17 |
| 14 | 17 |
| 7 | 25 |
| 6 | 25 |

EXAMPLE 20

Stabilisation of polybutadiene rubber (Brabender)

100 parts of polybutadiene (Diene ® 55, ex Firestone) and 0.25% of the stabiliser to be tested are kneaded in a Brabender plastograph at 160° C. and 60 rpm for 30 minutes. The induction time is measured from the flow of the torque, i.e. the time in minutes until the increase in torque after the minimum torque, which increase indicates the crosslinking of the rubber. The results are reported in Table 6.

TABLE 6

| Compound of Example | Induction time (in minutes) |
|---|---|
| without | 2.0 |
| 1 | 8.0 |
| 2 | 8.8 |

What is claimed is:

1. A composition comprising a lubricant or a hydraulic fluid and 0.01 to 5.0 wt.% of at least one compound of formula I

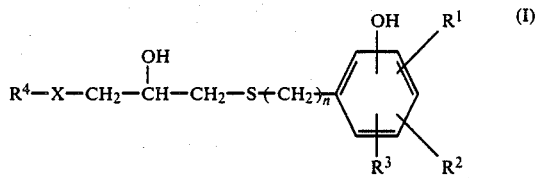

wherein X is —S—, —CH$_2$— or —NR$^5$—, where R$^5$ is hydrogen or C$_1$-C$_8$alkyl, n is 0, 1, 2 or 3, R$^1$ and R$^2$ are each independently of the other hydrogen or C$_1$-C$_{12}$alkyl, R$^3$ is hydrogen or methyl, and R$^4$ is C$_1$-C$_{22}$alkyl, C$_5$-C$_8$cycloalkyl, aryl or aryl which is substituted by one or two C$_1$-C$_8$alkyl radicals or is C$_7$-C$_{12}$aralkyl.

2. A composition according to claim 1, wherein X is —S— or —CH$_2$—, n is 0 or 1, R$^1$ and R$^2$ are each independently of the other hydrogen, methyl or tertiary C$_4$-C$_8$alkyl, R$^3$ is hydrogen and R$^4$ is C$_2$-C$_{12}$alkyl, C$_5$-C$_6$cycloalkyl, aryl or aryl substituted by one or two C$_1$-C$_4$alkyl radicals, or is C$_7$-C$_{10}$aralkyl.

3. A composition according to claim 1, wherein X is —S—.

4. A composition according to claim 1, wherein R$^4$ is C$_1$-C$_{22}$alkyl or C$_5$-C$_8$cycloalkyl.

5. A composition according to claim 1, wherein n is 0 or 1.

6. A composition according to claim 4, wherein R$^4$ is C$_4$-C$_{12}$alkyl.

7. A composition according to claim 1, wherein R$^1$ and R$^2$ are each independently of the other methyl or tert-butyl, and R$^3$ is hydrogen.

8. A composition according to claim 1, wherein the phenolic hydroxyl group is in the para-position relative to the thioether substituent.

9. A composition according to claim 1, wherein R$^1$ and R$^2$ are located in ortho-position to the phenolic hydroxyl group.

10. A composition according to claim 1, wherein X is —S— or —CH$_2$, n is 0 or 1, the phenolic hydroxyl group is in the para-position relative to the thioether substituent, R$^1$ and R$^2$ are located in positions ortho to the phenolic hydroxyl group and are each independently of the other C$_1$-C$_6$alkyl, R$^3$ is hydrogen, and R$^4$ is C$_2$-C$_{12}$alkyl or cyclohexyl.

11. A composition according to claim 1 which comprises a lubricant and at least one compound of formula I.

12. A compound of formula I

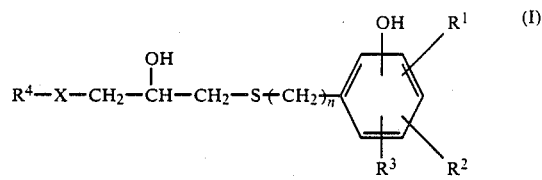

wherein X is —S— or —CH$_2$—, n is an integer having the value 0, 1, 2 or 3, R$^1$ and R$^2$ are each independently of the other hydrogen or C$_1$-C$_{12}$alkyl, R$^3$ is hydrogen or methyl, and R$^4$ is C$_1$-C$_{22}$alkyl, C$_5$-C$_8$cycloalkyl, aryl or aryl substituted by one or two C$_1$-C$_8$alkyl radicals, or is C$_7$-C$_{12}$aralkyl.

13. A compound according to claim 12, wherein n is 0 or 1, R$^1$ and R$^2$ are each independently of the other hydrogen, methyl or tertiary C$_4$-C$_8$alkyl, R$^3$ is hydrogen, and R$^4$ is C$_2$-C$_{12}$alkyl, C$_5$-C$_6$cycloalkyl, aryl or aryl substituted by one or two C$_1$-C$_4$alkyl radicals, or is C$_7$-C$_{10}$aralkyl.

14. A compound according to claim 12, wherein R$^4$ is C$_1$-C$_{22}$alkyl or C$_5$-C$_8$cycloalkyl.

15. A compound according to claim 12, wherein X is —S—.

16. A compound according to claim 13, wherein the phenolic hydroxyl group is in the para-position relative to the thioether substituent.

17. A compound according to claim 16, wherein R$^1$ and R$^2$ are each independently of the other methyl or tert-butyl and are located in both positions ortho to the phenolic hydroxyl group.

18. A compound according to claim 12, wherein n is 0 or 1, the phenolic hydroxyl group is in the para-position relative to the thioether substituent, R$^1$ and R$^2$ are located in the positions ortho to the phenolic hydroxyl group and are each independently of the other C$_1$-C$_6$alkyl, R$^3$ is hydrogen, and R$^4$ is C$_2$-C$_{12}$alkyl or cyclohexyl.

19. A method of improving the antioxidation, antiwear and extreme pressure properties of lubricants and hydraulic fluids, which comprises incorporating into said lubricants or hydraulic fluids an effective amount of a compound of formula I are as defined in claim 12.

20. A method of stabilising elastomers, which comprises incorporating into said elastomer with an effective amount of at least one compound of formula I as defined in claim 12.

21. A composition comprising an elastomer and 0.01 to 10 wt.% of at least one compound as defined in claim 12.

22. A composition according to claim 21, wherein the elastomer is a polydiene, a halogenated polymer or a polyurethane.

* * * * *